United States Patent
Brenner et al.

(10) Patent No.: US 6,235,738 B1
(45) Date of Patent: May 22, 2001

(54) DIPHENYL-SUBSTITUTED HETEROCYCLES WITH 6-MEMBERED RING, PROCESSES FOR THE PREPARATION THEREOF AND THE USE THEREOF AS MEDICAMENTS

(75) Inventors: Michael Brenner; Rainer Palluk, both of Bingen; Marion Wienrich, Weiterstadt; Thomas Weiser, Nieder-Olm, all of (DE); Enzo Cereda, Novi Ligure (IT); Maura Bignotti, Milan (IT); Carlo Maria Pellegrini, Casalpusterlengo (IT); Giovanni Battista Schiavi, Asola (IT); Raffaele Cesana, Milan (IT)

(73) Assignees: Boehringer Ingelheim Pharma KG, Ingelheim (DE); Boehringer Ingelheim Italia S.p.A., Florence (IT)

(*) Notice: Subject to any disclaimer, the term of this patent is extended or adjusted under 35 U.S.C. 154(b) by 0 days.

(21) Appl. No.: 09/290,335

(22) Filed: Apr. 12, 1999

(30) Foreign Application Priority Data

Apr. 17, 1998 (IT) .............................. MI98A0819

(51) Int. Cl.[7] .................. A61K 31/53; C07D 251/22; C07D 253/065; C07D 253/04
(52) U.S. Cl. ................. 514/241; 514/227.8; 514/236.2; 514/242; 544/60; 544/112; 544/113; 544/180; 544/182; 544/220
(58) Field of Search .................... 514/241, 242, 514/180; 544/182, 219, 220, 221, 222, 223

(56) References Cited

U.S. PATENT DOCUMENTS

| 3,821,221 | 6/1974 | Podesva et al. ............. 260/251 R |
| 3,969,355 | 7/1976 | Schwan ..................... 260/256.4 R |
| 5,521,189 | 5/1996 | Boykin et al. ............... 514/256 |

FOREIGN PATENT DOCUMENTS

| 0 086 411 A2 | 2/1983 | (EP) . |
| 0 635 500 A1 | 7/1994 | (EP) . |
| 0 713 703 A2 | 5/1996 | (EP) . |
| 0 781 766 A1 | 7/1997 | (EP) . |
| 98/17652 | 4/1998 | (WO) . |

OTHER PUBLICATIONS

Taylor et al., Chemical Abstract No. 110:135197, 1989.*
Brunetti et al., Chemical Abstract No. 67:91378, 1967.*
Konno et al., Chemical Abstract No. 122:180915, 1995.*
Pitet et al., Chemical Abstract No. 104:218618, 1986.*
Fabre, Chemical Abstract No. 90:121667, 1979.*
Kumar, A. et al.; "Anti–Pneumocystis carinii pneumonia activity of dicationic 2,4–diarylpyrimidines"; European Journal of Medicinal Chemistry.Chimica Therapeutica, Bd. 31, Nr. 10, Jan. 1, 1996 pp. 767–773.
Kuno, A. et al.; "Studies on Cerebral Protective Agents I.1) Novel 4–Aryipyrimidine Derivatives with Anti–anoxic and Anti–lipid Peroxidation Activities"; Chem., Pharm. Bull 1992, vol. 40, No. 6, pp. 1452–1461.

* cited by examiner

*Primary Examiner*—Mukund J. Shah
*Assistant Examiner*—Deepak R. Rao
(74) *Attorney, Agent, or Firm*—R. P. Raymond; A. R. Stempel; T. X. Witkowski

(57) ABSTRACT

The invention relates to novel diphenyl-substituted heterocycles with 6-membered ring of general formula (I)

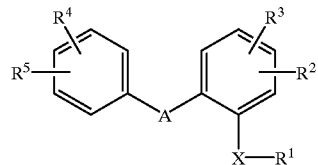

in which A, X and the residues $R^1$, $R^2$, $R^3$, $R^4$ and $R^5$ are as defined in the claims, processes for the preparation thereof and the use thereof as medicaments.

12 Claims, No Drawings

DIPHENYL-SUBSTITUTED HETEROCYCLES WITH 6-MEMBERED RING, PROCESSES FOR THE PREPARATION THEREOF AND THE USE THEREOF AS MEDICAMENTS

The invention relates to novel diphenyl-substituted heterocycles with 6-membered ring, processes for the preparation thereof and the use thereof as medicaments. The novel compounds have the structure of general formula (I):

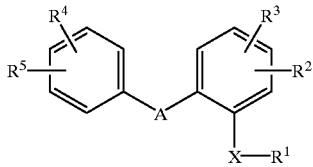

(I)

in which:
A is a 6-membered heterocycle, saturated or unsaturated, which can contain 1, 2 or 3 heteroatoms selected from the group of oxygen, nitrogen or sulfur, and is optionally substituted one or more times with —$OR^8$, =O or $C_1$–$C_6$-alkyl, wherein the $C_1$–$C_6$-alkyl residue can in its turn be substituted with halogen, hydroxy or —$NR^6R^7$;

X is oxygen, sulfur or $NR^6$;

$R^1$ is an $C_1$–$C_{10}$-alkyl, $C_2$–$C_{10}$-alkenyl or $C_2$–$C_{10}$-alkynyl residue, which can optionally be substituted one or more times with =O, —CN, —CHO, $C_6$–$C_{10}$-aryl, —$COOR^8$, —$CONHSO_2R^8$, —$CONR^6R^7$, —CH=$NOR^8$, —$COR^8$, —$NR^6R^7$, —$NHCOR^8$, —$NHCONR^6R^7$, —$NHCOOR^8$, —$OR^8$, —$OCOR^8$, —$OCOOR^8$, —$OCONR^6R^7$, —$SR^8$, —$SOR^8$, —$SO_2R^8$, $SO_3H$, —$SO_2NR^6R^7$, halogen or with a N-oxide of formula —$NOR^6R^7$; $R^2$ and $R^3$, which can be the same or different, are hydrogen, mercapto, —$NR^6R^7$, halogen, nitro, $CF_3$, CN, —$OR^8$, $C_1$–$C_{10}$-alkyl, $C_2$–$C_{10}$-alkenyl, $C_2$–$C_{10}$-alkynyl, $C_6$–$C_{10}$-aryl, $C_6$–$C_{10}$-aryl-($C_1$–$C_6$)alkyl-, or $C_6$–$C_{10}$-aryloxy;

$R^4$ and $R^5$ which can be the same or different, are hydrogen, mercapto, —$NR^6R^7$, halogen, nitro, $CF_3$, CN, —$OR^8$, $C_1$–$C_{10}$-alkyl, $C_2$–$C_{10}$-alkenyl, $C_2$–$C_{10}$-alkynyl, $C_6$–$C_{10}$-aryl, $C_6$–$C_{10}$-aryl-($C_1$–$C_6$)alkyl-, or $C_6$–$C_{10}$-aryloxy;

$R^6$ is hydrogen, $C_3$–$C_6$-cycloalkyl, $C_1$–$C_{10}$-alkyl, $C_2$–$C_{10}$-alkenyl or $C_2$–$C_{10}$-alkynyl, each of them being optionally substituted one or more times with phenyl, benzyl or —$OR^8$, or $R^6$ is $C_6$–$C_{10}$-aryl, preferably phenyl, which can optionally be substituted with halogen, —$OR^8$, $C_1$–$C_4$-alkyl, preferably with —$CH_3$, —$SO_3H$ or —$COOR^8$;

$R^7$ is hydrogen, $C_3$–$C_6$-cycloalkyl, $C_1$–$C_{10}$-alkyl, $C_2$–$C_{10}$-alkenyl or $C_2$–$C_{10}$-alkynyl, each of them being optionally substituted one or more times with phenyl, benzyl or —$OR^8$, or $R^7$ is $C_6$–$C_{10}$-aryl, preferably phenyl, which can optionally be substituted with halogen, —$OR^8$, $C_1$–$C_4$-alkyl, preferably with —$CH_3$, —$SO_3H$ or —$COOR^8$; or $R^6$ and $R^7$ together with the nitrogen atom form a 5- or 6-membered saturated or unsaturated ring, which can contain other heteroatoms such as nitrogen, oxygen or sulfur, wherein the heterocycle can be substituted with a branched or non-branched alkyl group with 1–4 carbon atoms, phenyl or benzyl;

$R^8$ is hydrogen, $C_1$–$C_4$-alkyl, $C_2$–$C_4$-alkenyl, $C_2$–$C_4$-alkynyl, a benzyl or phenyl residue, which is optionally substituted one or more times with OH, chlorine, bromine or $OCH_3$, optionally in the form of racemates, enantiomers, diastereomers and mixtures thereof, and optionally in the form of addition salts with pharmacologically acceptable acids.

Preferred are the compounds of general formula (I) in which:
A is a 6-membered heterocycle, saturated or unsaturated, which can contain 1, 2 or 3 nitrogen atoms, and is optionally substituted one or more times with =O or $C_1$–$C_4$-alkyl;

X is oxygen, sulfur or $NR^6$;

$R^1$ is an $C_1$–$C_6$-alkyl residue, which is optionally substituted one or more times with =O, —CN, —CHO, phenyl, —$COOR^8$, —$CONHSO_2R^8$, —$CONR^6R^7$, —CH=$NOR^8$, —$COR^8$, —$NR^6R^7$, —$NHCOR^8$, —$NHCONR^6R^7$, —$NHCOOR^8$, —$OR^8$, —$OCOR^8$, —$OCOOR^8$, —$OCONR^6R^7$, —$SR^8$, —$SOR^8$, —$SO_2R^8$, —$SO_3H$, —$SO_2NR^6R^7$, fluorine, chlorine, bromine or with a N-oxide of formula —$NOR^6R^7$;

$R^2$ and $R^3$ which can be the same or different, are hydrogen, SH, —$NR^6R^7$, fluorine, chlorine, bromine, nitro, $CF_3$, CN, —$OR^8$, $C_1$–$C_6$-alkyl, $C_2$–$C_6$-alkenyl, $C_2$–$C_6$-alkynyl, phenyl, benzyl or phenyloxy;

$R^4$ and $R^5$ which can be the same or different, are hydrogen, SH, —$NR^6R^7$, fluorine, chlorine, bromine, nitro, $CF_3$, CN, —$OR^8$, $C_1$–$C_6$-alkyl, $C_2$–$C_6$-alkenyl, $C_2$–$C_6$-alkynyl, phenyl, benzyl or phenyloxy;

$R^6$ is hydrogen, $C_3$–$C_6$-cycloalkyl, $C_1$–$C_6$-alkyl, $C_2$–$C_6$-alkenyl or $C_2$–$C_6$-alkynyl, each of them being optionally substituted one or more times with hydroxy, phenyl, benzyl or $C_1$–$C_4$-alkoxy, or $R^6$ is phenyl, which can optionally be substituted with fluorine, chlorine, bromine, —$OR^8$, $C_1$–$C_4$-alkyl, preferably with —$CH_3$, —$SO_3H$ or —$COOR^8$;

$R^7$ is hydrogen, $C_3$–$C_6$-cycloalkyl, $C_{1-C6}$-alkyl, $C_2$–$C_6$-alkenyl or $C_2$–$C_6$-alkynyl, each of them being optionally substituted one or more times with hydroxy, phenyl, benzyl or $C_1$–$C_4$-alkoxy, or $R^7$ is phenyl, which can optionally be substituted with fluorine, chlorine, bromine, —$OR^8$, $C_1$–$C_4$-alkyl, preferably with —$CH_3$, —$SO_3H$ or —$COOR^8$; or $R^6$ and $R^7$ together with the nitrogen atom form a 5- or 6-membered saturated or unsaturated ring, which can contain other heteroatoms such as nitrogen or oxygen, wherein the heterocycle can be substituted with $C_1$–$C_4$-alkyl, phenyl or benzyl;

$R^8$ is hydrogen, $C_1$–$C_4$-alkyl, $C_2$–$C_4$-alkenyl, $C_2$–$C_4$-alkynyl, a benzyl or phenyl residue, which is optionally substituted one or more times with OH, chlorine, bromine or $OCH_3$, optionally in the form of racemates, enantiomers, diastereomers and mixtures thereof, and optionally in the form of addition salts with pharmacologically acceptable acids.

Particularly preferred are the compounds of general formula (I) in which:
A is a 6-membered heterocycle, saturated or unsaturated, which can contain 1, 2 or 3 nitrogen heteroatoms, and is optionally substituted one or more times with =O or $C_1$–$C_4$-alkyl;

X is oxygen;

$R^1$ is an $C_1$–$C_4$-alkyl residue, which is substituted with —$CONHSO_2R^8$, —$CONR^6R^7$, —CH=$NOR^8$, —$NR^6R^7$, —$NHCOR^8$, —$NHCONR^6R^7$, —$NHCOOR^8$, —$OCONR^6R^7$, —$SO_2NR^6R^7$, or with a N-oxide of formula —$NOR^6R^7$;

$R^2$ and $R^3$ which can be the same or different, are hydrogen, —$NR^6R^7$, fluorine, chlorine, bromine, nitro, $CF_3$, CN, —$OR^8$, $C_1$–$C_4$-alkyl, phenyl, benzyl or phenyloxy;

$R^4$ and $R^5$ which can be the same or different, are hydrogen, —$NR^6R^7$, fluorine, chlorine, bromine, nitro, $CF_3$, CN, —$OR^8$, $C_1$–$C_4$-alkyl, phenyl, benzyl or phenyloxy;

$R^6$ is hydrogen, $C_3$–$C_6$-cycloalkyl or $C_1$–$C_4$-alkyl, each of them being optionally substituted one or more times with hydroxy, phenyl, benzyl or $C_1$–$C_4$-alkoxy, or $R^6$ is phenyl, which can optionally be substituted with fluorine, chlorine, bromine, —$OR^8$, $C_1$–$C_4$-alkyl, preferably with —$CH_3$, —$SO_3H$ or —$COOR^8$;

$R^7$ is hydrogen, $C_3$–$C_6$-cycloalkyl or $C_1$–$C_4$-alkyl, each of them being optionally substituted one or more times with hydroxy, phenyl, benzyl or $C_1$–$C_4$-alkoxy, or $R^7$ is phenyl, which can optionally be substituted with fluorine, chlorine, bromine, —$OR^8$, $C_1$–$C_4$-alkyl, preferably with —$CH_3$, —$SO_3H$ or —$COOR^8$; or $R^6$ and $R^7$ together with the nitrogen atom form a 5- or 6-membered ring, saturated or unsaturated, which can contain other heteroatoms such as nitrogen or oxygen, wherein the heterocycle can be substituted with $C_1$–$C_4$-alkyl, phenyl or benzyl;

$R^8$ is hydrogen, $C_1$–$C_4$-alkyl, a benzyl or phenyl residue, which is optionally substituted one or more times with OH, chlorine, bromine or $OCH_3$, optionally in the form of racemates, enantiomers, diastereomers and mixtures thereof, and optionally in the form of the addition salts with pharmacologically acceptable acids.

Most preferred are the compounds of general formula (I), in which:

A is a 6-membered heterocycle, saturated or unsaturated, which can contain 1, 2 or 3 nitrogen heteroatoms, and is optionally substituted one or more times with =O or $C_1$–$C_4$-alkyl;

X is oxygen;

$R^1$ is $C_1$–$C_4$-alkyl, which is substituted with —$NR^6R^7$ or with a N-oxide of formula —$NOR^6R^7$;

$R^2$ and $R^3$ are hydrogen;

$R^4$ and $R^5$ are hydrogen;

$R^6$ is hydrogen or $C_1$–$C_4$-alkyl;

$R^7$ is hydrogen or $C_1$–$C_4$-alkyl; or $R^6$ and $R^7$ together with the nitrogen atom form a saturated or unsaturated ring, selected from the group consisting of pyrrole, pyrroline, pyrrolidine, piperidine, piperazine, morpholine, thiomorpholine, imidazole, imidazoline, imidazolidine, pyrazole, pyrazoline, pyrazolidine, wherein the cited heterocycles can optionally be substituted with methyl, ethyl, propyl or benzyl; optionally in the form of racemates, enantiomers, diastereomers and mixtures thereof, and optionally in the form of addition salts with pharmacologically acceptable acids.

Particularly important are the compounds of general formula (I) in which:

A is a 6-membered heterocycle, selected from the group consisting of pyridine, pyridazine, pyrimidine, pyrazine or triazine, which can optionally be substituted with =O or $C_1$–$C_4$-alkyl;

X is oxygen;

$R^1$ is methyl, ethyl or propyl, each of them is substituted with —$NR^6R^7$ or with a N-oxide of formula —$NOR^6R^7$;

$R^2$ and $R^3$ are hydrogen;

$R^4$ and $R^5$ are hydrogen;

$R^6$ is hydrogen, methyl, ethyl or propyl;

$R^7$ is hydrogen, methyl, ethyl or propyl; optionally in the form of racemates, enantiomers, diastereomers and mixtures thereof, and optionally in the form of the addition salts with pharmacologically acceptable acids.

Furthermore, particularly important are the compounds of general formula (I), in which the group:

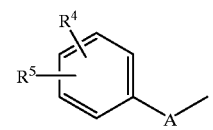

is one of the following residues:

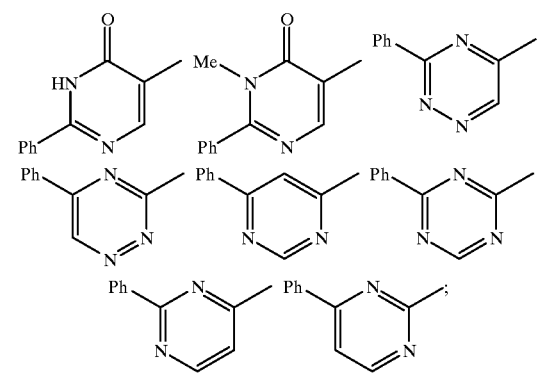

X is oxygen;

$R^1$ is ethyl or propyl, each of them being substituted with —$NR^6R^7$;

$R^2$ and $R^3$ are hydrogen;

$R^6$ is methyl, ethyl or propyl;

$R^7$ is methyl, ethyl or propyl; optionally in the form of racemates, enantiomers, diastereomers and mixtures thereof, and optionally in the form of the addition salts with pharmacologically acceptable acids. Moreover, particularly important are the compounds of general formula (I), in which the group:

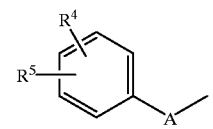

is one of the following residues:

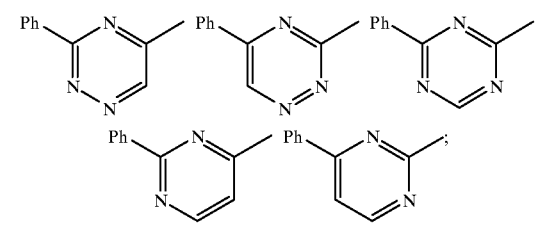

X is oxygen;

$R^1$ is —CH$_2$—CH$_2$—NR$^6$R$^7$;

$R^2$ and $R^3$ are hydrogen;

$R^6$ is methyl;

$R^7$ is methyl, optionally in the form of racemates, enantiomers, diastereomers and mixtures thereof, and optionally in the form of the addition salts with pharmacologically acceptable acids.

According to the invention, the following compounds are particularly important:

5-{2-[2-(N,N-Dimethylamino)ethyl]oxy-phenyl}-3-phenyl-1,2,4-triazine

3-{2-[2-(N,N-Dimethylamino)ethyl]oxy-phenyl}-5-phenyl-1,2,4-triazine

2-{2-[2-(N,N-Dimethylamino)ethyl]oxy-phenyl}-4-phenyl-1,3,5-triazine, and

4-{2-[2-(N,N-Dimethylamino)ethyl]oxy-phenyl}-2-phenyl-pyrimidine.

The term alkyl groups (also when they are part of other residues such as alkylene bridges) are, if not otherwise stated, branched and non-branched alkyl groups with 1–10 carbon atoms, preferably with 1–4 carbon atoms; such as: methyl, ethyl, n-propyl, iso-propyl, butyl, iso-butyl, sec-butyl, tert-butyl, pentyl, iso-pentyl, hexyl, heptyl and octyl. Methyl, ethyl, butyl and tert-butyl are also indicated with the abbreviations Me, Et, Bu or tBu.

Substituted alkyl groups, if not otherwise stated, (also when they are part of other residues), can have for example one or more of the following substituents: halogen, hydroxy, mercapto, alkoxy(C$_1$–C$_6$), amino, alkylamino, dialkylamino, cyano, nitro, =O, —CHO, —COOH, —COO-C$_1$–C$_6$-alkyl, —S—C$_1$–C$_6$-alkyl.

The term alkenyl groups (also when they are part of other residues) are branched and non-branched alkenyl groups with 2–10 carbon atoms, preferably with 2–3 carbon atoms, provided they have at least one double bond, for example also the alkyl groups cited above provided they have at least one double bond, such as vinyl (as far as enamines or unstable enol ethers do not form), propenyl, iso-propenyl, butenyl, pentenyl, hexenyl.

Substituted alkenyl groups, if not otherwise stated, (also when they are part of other residues), can have for example one or more of the following substituents: halogen, hydroxy, mercapto, alkoxy(C$_1$–C$_6$), amino, alkylamino, dialkylamino, cyano, nitro, =O, —CHO, —COOH, —COO-C$_1$–C$_6$-alkyl, —S—C$_1$–C$_6$-alkyl.

The term alkynyl groups (also when they are part of other residues) are alkynyl groups with 2–10 carbon atoms, provided they have at least one triple bond, for example ethynyl, propargyl, butenyl, pentenyl, hexenyl.

Substituted alkynyl groups, if not otherwise stated, (also when they are part of other residues), can have for example one or more of the following substituents: halogen, hydroxy, mercapto, alkoxy(C$_1$–C$_6$), amino, alkylamino, dialkylamino, cyano, nitro, =O, —CHO, —COOH, —COO-C$_1$–C$_6$-alkyl, —S—C$_1$–C$_6$-alkyl.

C$_3$–C$_6$-cycloalkyl residues are, for example, cyclopropyl, cyclobutyl, cyclopentyl or cyclohexyl, which can also be substituted with branched or non-branched alkyl with 1–4 carbon atoms, hydroxy and/or halogen or as defined above.

Halogen usually means fluorine, chlorine, bromine or iodine.

The term aryl means an aromatic ring system with 6–10 carbon atoms which, if not otherwise stated, can have for example one or more of the following substituents: C$_1$–C$_6$-alkyl, C$_1$–C$_6$-alkoxy, halogen, hydroxy, mercapto, amino, alkylamino, dialkylamino, CF$_3$, cyano, nitro, —CHO, —COOH, —COO-C$_1$–C$_6$-alkyl, —S—C$_1$–C$_6$-alkyl. The preferred aryl residue is phenyl. Examples of cyclic residues linked with the nitrogen of general formula NR$^6$R$^7$, are: pyrrole, pyrroline, pyrrolidine, 2-methylpyrrolidine, 3-methylpyrrolidine, piperidine, piperazine, N-methylpiperazine, N-ethylpiperazine, N-(n-propyl)-piperazine, N-benzylpiperazine, morpholine, thiomorpholine, imidazole, imidazoline, imidazolidine, pyrazole, pyrazoline, pyrazolidine, preferably morpholine, N-benzylpiperazine, piperazine and piperidine, wherein the cited heterocycles can be substituted with alkyl with 1–4 carbon atoms, preferably with methyl.

=O is an oxygen atom linked with a double bond.

The present invention discloses compounds which surprisingly have a high affinity for the following type of receptor: "Na$^+$ canal site 2" binding site. Moreover these compounds show antagonistic activity on the AMPA receptor, therefore the compounds according to the invention can be used in neurodegenerative diseases and in cerebral ischemia of different genesis.

The compounds according to the invention can be prepared with methods analogous to known processes. Thus, for example, compounds of general formula (II)

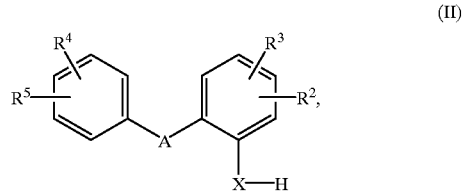

(II)

in which A, X and the residues $R^2$, $R^3$, $R^4$ and $R^5$ have the meanings defined above, are alkylated in basic conditions with electrophiles of general formula

L —R$^1$ in which L is a leaving group such as chlorine, bromine, iodine, methanesulfonyl, trifluoromethanesulfonyl or p-toluenesulfonyl, and R$^1$ has the meaning defined above, to obtain the compounds of general formula (I).

The following preparation procedures illustrate in greater detail the processes which can be used for the preparation of the compounds according to the invention, without limiting the scope of the invention.

EXAMPLE 1

4-(2-Hydroxyphenyl)-6-phenyl-pyrimidine

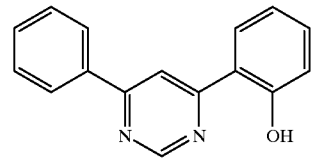

A solution of 1-(2-hydroxy-phenyl)-3-phenyl-1,3-propanedione (4 g) in formamide (40 ml) was heated at 170° C. under stirring for 3 hours. The solution was cooled, then poured into water and extracted repeatedly with diethyl ether. The organic phase was dried, evaporated to dryness and the resulting residue was purified by flash chromatography (eluent cyclohexane/ethyl acetate 80:20).

EXAMPLE 2

4-{2-[2-(N,N-Dimethylamino)ethyl]oxy-phenyl}-6-phenyl-pyrimidine

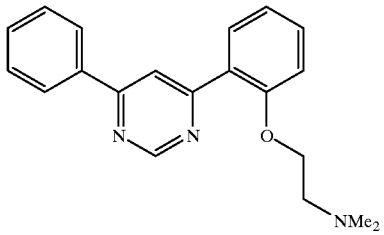

A solution of 4-(2-hydroxyphenyl)-6-phenyl-pyrimidine (0.5 g, example 1) and sodium hydride (0.12 g, 80% in oil) in anhydrous dimethylformamide (5 ml) was stirred 20 minutes at room temperature. Then 2-dimethylaminoethyl chloride hydrochloride (0.29 g) was added and the solution was heated at 100° C. under stirring for 6 hours. The reaction mixture was cooled, then poured into water, and the separated oil was extracted with ethyl acetate. The organic layer was dried, then evaporated to dryness to give 500 mg of the title compound as a crude residue, which was purified through its hydrochloride salt. This was obtained by dissolving the free base in acetone, adding a hydrochloric acid ethereal solution and filtering off the crystallized salt.

Yield: 0.4 g. Melting point: 135–140° C. with decomposition (as hydrochloride salt, from acetone).

EXAMPLE 3

4-(2-Hydroxyphenyl)-2-phenyl-pyrimidine

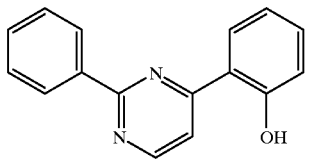

A solution of 3-bromo-chroman-4-one (2.5 g) and benzydamine hydrochloride (1.7 g) in dry ethanol (25 ml) was refluxed for 6 hours in the presence of DBU (1.7 g). The reaction mixture was cooled, then evaporated to dryness and the residue was partitioned between ethyl acetate and a diluted hydrochloric acid aqueous solution. The organic layer was washed with a diluted sodium carbonate aqueous solution, with water, dried and evaporated to dryness to give the crude title compound. This was purified through its hydrochloride, prepared by dissolving the free base in acetone and adding an HCl ethereal solution.

Yield: 0.85 g. Melting point: 195–198° C. with decomposition (as hydrochloride, from acetone)

EXAMPLE 4

4-{2-[2-(N,N-Dimethylamino)ethyl]oxy-phenyl}-2-phenyl-pyrimidine

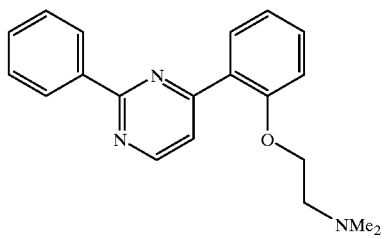

The preparation was carried out starting from 4-(2-hydroxyphenyl)-2-phenyl-pyrimidine (example 3) as described in example 2.

Melting point: 210–215° C. with decomposition (as hydrochloride, from acetone)

EXAMPLE 5

2-{2-[2-(N,N-Dimethylamino)ethyl]oxy-phenyl}4-phenyl-pyrimidine

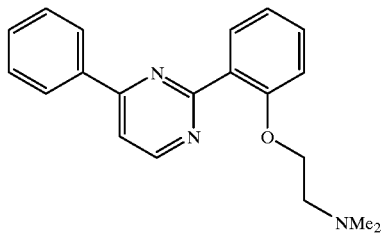

The preparation was carried out analogously to examples 2 and 4.

EXAMPLE 6

2-{2-[2-(N,N-Dimethylamino)ethyl]oxy-phenyl}-4-phenyl-1,3,5-triazine

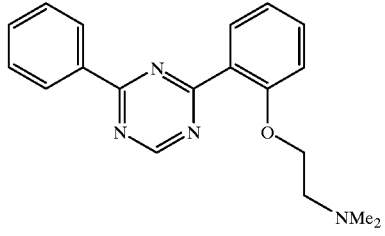

a) 2-(2-Dimethylamino-ethoxy)-benzamide

A solution of 2-hydroxy-benzamide (10 g) and potassium carbonate (35.4 g) in dioxane (50 ml) and water (4.5 ml) was added with N,N-dimethyl-2-chlorethylamine hydrochloride (6.5 g). The mixture was heated at 85° C. for 3 hours. The solvent was evaporated off, the resulting residue was poured into 5% HCl and extracted with diethyl ether. The aqueous phase was adjusted to pH with sodium bicarbonate, then extracted with ethyl acetate. The organic layer was dried and evaporated to dryness to give the title compound as a white solid (5.7 g).

b) 2-(2-Dimethylaminoethoxy)-N,N-dimethylaminomethylene benzamide;

A mixture of 2-(2-dimethylamino-ethoxy)-benzamide (3 g) and N,N-dimethylformamide dimethylacetal (4.2 ml) was stirred at 110–120° C. for 3 hours. The formed methanol was distilled off under atmospheric pressure, followed by high vacuum distillation. The title compound (light oil) was used without further purification.

c) 2-{2-[2-(N,N-Dimethylamino)ethyl]oxyphenyl}-4-phenyl-1,3,5-triazine

A solution of 2-(2-dimethylamino-ethoxy)-N,N-dimethylamino-methylene benzamide (4 g) in dry tetrahydrofuran was added under nitrogen with benzydamine hydrochloride (2.34 g) and potassium tert-butoxide (1.68 g). The mixture was stirred at 55° C. for 3 hours, the solvent was evaporated off and the crude product was purified by column chromatography on neutral alumina (eluent: n-hexane/ethyl acetate 1:1), to obtain the title compound as an oil; this was then dissolved in ethyl acetate and added with the suitable amount of oxalic acid. The oxalate salt of the title compound was obtained as a white solid.

Yield: 0.2 g. Melting point: 126–129° C. with decomposition.

EXAMPLE 7

5-{2-[2-(N,N-Dimethylamino)ethyl]oxy-phenyl}-3-phenyl-1,2,4-triazine

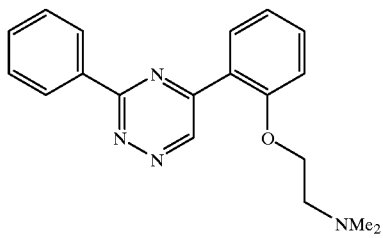

a) 1-[2-(2-Dimethylamino-ethoxy)-phenyl]-ethanone

The preparation was carried out starting from 1-(2-hydroxyphenyl)ethanone analogously to example 6, step a.

b) [2-(2-Dimethylamino-ethoxy)-phenyl]-oxo-acetaldehyde

A solution of 1-[2-(2-dimethylamino-ethoxy)-phenyl]-ethanone (4.35 g) in dimethylsulfoxide (8.8 ml) was added with 48% HBr (1.8 ml). The mixture was stirred at 80° C. for 6 hours under nitrogen stream. Then it was poured into methylene chloride (50 ml) and dried over magnesium sulfate. The mixture was neutralized to pH 7 with solid sodium bicarbonate, then filtered and evaporated under high vacuum at low temperature. The title compound was used without further purification.

c) 5-{2-[2-(N,N-Dimethylamino)ethyl]oxy-phenyl}-3-phenyl-1 2,4-triazine

A solution of benzocarboxyimidic acid hydrazide (0.9 g) in methanol (10 ml) at 5° C. was slowly added to a solution of [2-(2-dimethylamino-ethoxy)-phenyl]-oxo-acetaldehyde in methanol (1.4 g). The mixture was stirred at 5° C. for 6 hours. The solvent was evaporated off under vacuum, and the crude product was purified by flash chromatography on silica gel (eluent: methylene chloride/methanol/aqueous ammonia 95:5:0.5), to obtain the title compound as a brown oil. This was dissolved in ethyl acetate and added with the suitable amount of oxalic acid, to give the oxalate salt of the title compound as a pale yellow solid.

Yield: 0.240 g. Melting point: 167–170° C.

EXAMPLE 8

3-{2-[2-(N,N-Dimethylamino)ethyl]oxy-phenyl}-5-phenyl-1,2,4-triazine

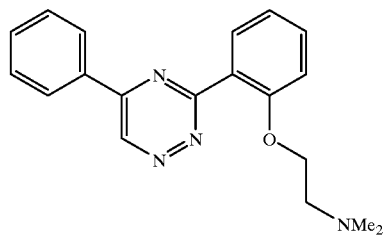

a) 2-(2-Dimethylamino-ethoxy)-benzonitrile

The preparation was carried out starting from 2-hydroxybenzonitrile, analogously to example 6, step a.

b) 2-(2-Dimethylamino-ethoxy)-thiobenzamide

A mixture of trimenthylsilyl sulfide (5 g) and sodium methoxide (1.5 g) was added drop by drop to a stirred solution of 2-(2-dimethylamino-ethoxy)-benzonitrile (2.66 g) in 1,3-dimethyl-2-imidazolidinone. The mixture was stirred at room temperature for 24 hours, then extracted with ethyl acetate and the organic layer was washed with water, dried over magnesium sulfate and evaporated. The crude product was used without further purification.

c) 2-(2-Dimethylamino-ethoxy)-benzocarboxyimidic acid hydrazide

A solution of 2-(2-dimethylamino-ethoxy)-thiobenzamide (9.4 g) in methanol (50 ml) was slowly added with an 85% hydrazine hydrate aqueous solution (2.45 ml). The mixture was stirred at room temperature for 4 hours, then the solvent was evaporated off, and the crude product was purified by flash chromatography on silica gel (eluent methylene chloride/methanol/aqueous ammonia 80:20:2), to give the title compound (1.2 g) as a brown oil.

d) 3-{2-[2-(N,N-Dimethylamino)ethyl]oxy-phenyl}-5-phenyl-1,2,4-triazine

A solution of 2-(2-dimethylamino-ethoxy)-benzocarboxyimidic acid hydrazide (1.2 g) in methanol (10 ml) at 5° C. was slowly added with a solution of phenylglyoxal hydrate (0.82 g) in methanol (8 ml). The mixture was stirred at 5° C. for 2 hours, then the solvent was evaporated off under vacuum, and the crude product was purified by column chromatography on silica gel (eluent: methylene chloride/methanol/aqueous ammonia 90:10:1), to give the title compound as a yellow oil. This was dissolved in ethyl acetate and added with the suitable amount of oxalic acid, to give the oxalate salt of the title compound as a pale yellow solid.

Yield: 0.260 g. Melting point: 175–180° C. with decomposition.

EXAMPLE 9

5-(2-Methoxyphenyl)-2-phenyl-3H-pyrimidin-4-one

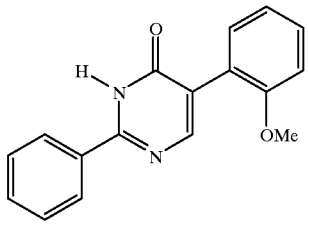

A mixture of ethyl 2-methoxy-phenylacetic acid ethyl ester (11 g), ethyl formate (8.2 ml) and sodium (1.5 g) was added drop by drop with ethanol (5 ml) at 0° C., and the resulting mixture was stirred for 2 days at room temperature. Water was added, the organic layer was separated, the aqueous phase was washed with diethyl ether and extracted three times with ethyl acetate. The combined extracts were washed with water, dried and evaporated, to give 2 g of ethyl 2-(2-methoxy-phenyl)-3-oxo-propionate. The compound described above (2 g) was dissolved in water (50 ml), added with sodium carbonate (0.95 g), and the resulting mixture was added drop by drop with a solution of benzydamine (1.1 g) in water. The mixture was then heated under stirring for 10 hours at 60° C., acidified and extracted 3 times with methylene chloride. The combined extracts were washed with an 8% sodium bicarbonate aqueous solution, with water, dried and evaporated. The solid residue was crystallized from diethyl ether, to give the title product as a white solid (0.4 g).

Melting point: 245–247° C.

EXAMPLE 10

5-(2-Methoxyphenyl)-3-methyl-2-phenyl-pyrimidin-4-one

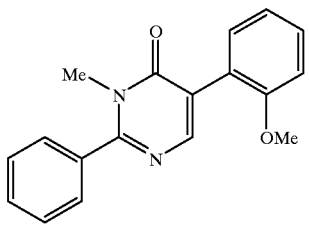

A mixture of 5-(2-methoxyphenyl)-2-phenyl-3H-pyrimidin-4-one (0.4 g, example 9), methyl iodide (0.134 ml), potassium carbonate (0.398 g) and tetrabutylammonium bromide (0.048 g) in toluene (60 ml) and water (10 ml) was refluxed for 2 hours and then evaporated. The residue was taken up in diethyl ether and insolubles were filtered off. The ether solution was evaporated, and the residue was purified by flash chromatography on silica gel (eluent: n-hexane/ethyl acetate 6:4), to give the title compound in a pure form as a white solid (0.22 g).

Melting point: 119–120° C.

It has surprisingly been found that the compounds of the invention show affinity for different types of receptors or activity on them, and have a neuroprotective effect.

It has been proved both in vitro and in vivo that cell damage and the disfunctions occurring in brain following hypoglicemia, hypoxia, anoxia, global and local ischemia, head trauma, cerebral oedema and cerebral hypertension are partly connected with an increase in synaptic activity, and therefore with an increase in the released transmitters. Besides glutamate, histamine and serotonin are particularly important as neurotransmitters. Moreover, concentrations of calcium and sodium ions are altered.

It is known that, following systemic administration of glutamate, mice brain neurons are destroyed (S. M. Rothman and T. W. Olney, Trends in Neurosciences 10(1987) 299). Such a result leads to the conclusion, inter alia, that glutamate plays a role in neurodegenerative diseases (R. Schwarcz and B. Meldrum, The Lancet 11(1985) 140). Moreover some substances, such as quisqualinic acid, kainic acid, ibotenic acid, glutamic acid, N-methyl-D-aspartic acid (NMDA) and alfa-amino-3-hydroxy-5-methyl-4-isoxazol-propionic acid (AMPA), are known to be exogenous or endogenous neurotoxins. Cerebral lesions which can be induced by these substances are comparable with those occurring in epilepsy and other neurodegenerative diseases, such as Huntington's disease and Alzheimer's disease. The substances and the ions which inhibit the activity of glutamate receptors and of the ionic canal related to this receptor, such as competitive and non-competitive antagonists of eccitatory amino acids, have a protective action on brain cells against damages induced by hypoxia or ischemia. These results show that glutamate receptors have an important role in mediating cerebral damage.

The effected on AMPA receptor was tested by electrophysiology on neuronal cells (Patch-Clamp method) (M. L. Mayer, L. Vyklicky and G. L. Westbrook, J. Physiol. 415(1989) 329–350).

TABLE 1

Inhibition of the signal induced by kainate on AMPA receptor

| example | AMPA Inh. [%] |
|---|---|
| 4 | 96 |
| 6 | 66 |
| 7 | 98 |
| 8 | 95 |

The test of affinity for the "$Na^+$ canal site 2" binding site was carried out as described by G. B. Brown (J. Neurosci. 6 (1986) 2064). Tests were carried out typically at a test concentration of 10 $\mu$M.

TABLE 2

| example | Ki [$\mu$m] |
|---|---|
| 4 | 4 |
| 6 | 2,8 |
| 7 | 2,4 |

The results described above prove that the compounds of general formula (I) can be used in neurodegenerative diseases and in cerebral ischemia of different genesis. Among these, can be cited: status epilepticus, hypoglycemia, hypoxia, anoxia, head trauma, cerebral oedema, amyotrophic lateral sclerosis, Huntington's disease, Alzheimer's disease, hypotonia, cardiac infarction, cerebral hypertension (too high intracranial pressure), ischemic and hemorrhagic syndromes, complete cerebral ischemia in cardiac arrest, diabetic polyneuropathy, tinnitus, asphyxia neonatorum, psychosis, schizophrenia, depression and Parkinson's disease.

The compounds of general formula (I) can be used alone or in combination with other active substances according to the invention, optionally also in combination with other pharmacologically active substances. Suitable administration forms are, for example, tablets, capsules, patches, solutions, in particular solutions for injection (subcutaneous, intravenous, intramuscular) and solutions for infusion, emulsions or dispersible powders.

The amount of pharmaceutically active compound(s) should be, in any case, within the range of 0.1 to 90% by weight, preferably 0.5 to 50% on the total weight composition, i.e. should be in a sufficient amount to lie in the above indicated range. Tablets can be obtained for example by mixing the active substance(s) with known auxiliaries, for example inert diluents, such as calcium carbonate, calcium phosphate or lactose; disintegrants, such as maize starch or alginic acid; binders, such as starch or gelatin; lubricants, such as magnesium stearate or talc, and/or prolonged-release agents, such as carboxymethylcellulose, cellulose acetate phthalate or polyvinyl acetate. Tablets can be multi-coated.

Sugar-coated pills can be prepared by coating cores prepared analogously to tablets with conventional agents, for example collidone or shellac, gum arabic, talc, titanium dioxide or sugar. A multi-coated core can be used to obtain a delayed effect or to avoid incompatibility. Similarly, the outer coat of the sugar-coated pill can also be multi-coated, to obtain a delayed effect; in this case, the auxiliaries cited above for the tablets can be used.

Syrups of the active substances according to the invention or of combinations of active substances can further contain a sweetener, such as saccharin, cyclamate, glycerin or sugar, as well a taste masking agents, for example, a flavoring agent, such as vanillin or orange flavor. Syrups can also contain auxiliary suspending agents or thickening agents, such as sodium carboxymethylcellulose, surfactants, for example condensation products of fatty alcohols with ethylene oxide, or preservatives, such as p-hydroxybenzoate.

Solutions for injection and for infusion are prepared conventionally, for example adding osmolality agents, preservatives, such as p-hydroxybenzoates, or stabilizers, such as ethylenediamino-tetraacetic acid alkaline salts, optionally with use of emulsifiers and/or dispersants; when using, for example, water as the diluent, organic solvents can optionally be used as mixing agents or solubilizers, and place the solution in ampoules for injection or in vials or ampoules for infusion.

The capsules containing one or more active substances or combinations of active substances can be prepared, for example, mixing the active substance with inert carriers, such as lactose or sorbite, and placing the mass in gelatin capsules. Suitable suppositories can be prepared, for example, by admixture with suitable carriers, such as neutral fat or polyethylene glycol, or derivatives thereof.

As auxiliary substances can be cited, for example, water, pharmaceutically acceptable organic solvents, such as paraffins (for example petroleum fractions), vegetable oils (for example peanut or sesame oil), mono- or poly- alcohols (for example ethanol or glycerin), carriers such as natural mineral powders (for example kaolin, alumina, talc, gypsum), synthetic mineral powders (for example highly dispersed silicic acid and silicates), sugars (for example saccharose, lactose and grape sugar), emulsifiers (for example lignin, sulfite spent lye, starch and polyvinylpyrrolidone) and lubricants (for example magnesium stearate, talc, stearic acid and sodium laurylsulfate).

The administration is carried out conventionally, preferably through the parenteral route, more particularly by infusion in the case of the intravenous route. For the oral administration, tablets can also contain, in addition to the cited carriers, excipients such as sodium citrate, calcium carbonate and dicalcium phosphate, together with fillers such as starch, preferably potato starch, gelatin and the like. Moreover, for the preparation of tablets, lubricants can be added, such as magnesium stearate, sodium laurylsulfate and talc. In the case of aqueous suspensions, the active substances can also be treated, in addition to the auxiliaries already cited, with taste masking agents or dyes. For the parenteral administration, the solutions of active substances can be used together with suitable liquid carriers. The dosage for the intravenous administration is 1–1000 mg per hour, preferably 5 to 500 mg per hour.

However, it could be necessary to depart from the cited amounts, depending on the body weight or on the administration route, on the individual response to the medicament, on the type of formulation and on the time, or time range, in which the administration is carried out. Therefore, it can be sufficient, in some cases, to use a lower amount then the cited minimum amount, whereas in other cases the higher range could be exceeded. When administering higher amounts, it would be advisable to subdivide them in repeated administrations during the day. Moreover, the compounds of general formula I or the acid addition salts thereof can also be combined with other, different active substances.

The following examples illustrate the present invention, without limiting the scope thereof.

Examples of pharmaceutical formulation

| A) Tablets | for tablet |
|---|---|
| Active substance | 100 mg |
| Lactose | 140 mg |
| Maize starch | 240 mg |
| Polyvinylpyrrolidone | 15 mg |
| Magnesium stearate | 5 mg |
|  | 500 mg |

The finely ground active substance, lactose are part of maize starch are mixed. The mixture is sieved, wetted with a solution of polyvinylpyrrolidone in water, kneaded, finely granulated and dried. The granulate, the remaining maize starch and magnesium stearate are sieved and mixed together. The mixture is compressed to tablets of suitable form and size.

| B) Tablets | for tablet |
|---|---|
| Active substance | 80 mg |
| Lactose | 55 mg |
| Maize starch | 190 mg |
| Microcrystalline cellulose | 35 mg |
| Polyvinylpyrrolidone | 15 mg |
| Sodium carboxymethyl starch | 23 mg |
| Magnesium stearate | 2 mg |
|  | 400 mg |

The finely ground active substance, part of the maize starch, lactose, microcrystalline cellulose and polyvinylpyrrolidone are mixed. The mixture is sieved and worked up with the remaining maize starch and water, to obtain a granulate, which is dried and sieved. This is added with sodium carboxymethyl starch and magnesium stearate and mixed, then the mixture is compressed to tablets of suitable size.

| C) | |
|---|---|
| Solution for vials | |
| Active substance | 50 mg |
| Sodium chloride | 50 mg |
| Water for injection | 5 ml |

The active substance is dissolved in water, optionally at pH of 5.5 to 6.5, and treated with sodium chloride as an osmolality agent. The resulting solution is filtered apyrogenically, and the filtrate is placed in vials under asepsis conditions, then vials are sterilized and flame sealed. The vials contain 5 mg, 25 mg and 50 mg of active substance.

What is claimed is:

1. A compound of the formula (I):

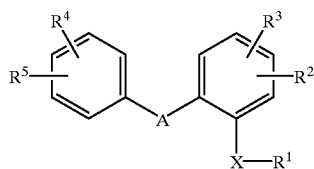

(I)

wherein:
A is a triazine optionally substituted one or more times with $=O$ or $C_1$–$C_4$-alkyl;
X is oxygen;
$R^1$ is an $C_1$–$C_4$-alkyl residue substituted with —$CONHSO_2R^8$, —$CONR^6R^7$, —$CH=NOR^8$, —$NR^6R^7$, —$NHCOR^8$, —$NHCONR^6R^7$, —$NHCOOR^8$, —$OCONR^6R^7$, —$SO_2NR^6R^7$, or with an N-oxide of formula —$NOR^6R^7$;
$R^2$ and $R^3$ which can be the same or different, are hydrogen, —$NR^6R^7$, fluorine, chlorine, bromine, nitro, —$CF_3$, —CN, —$OR^8$, $C_1$–$C_4$-alkyl, phenyl, benzyl, or phenyloxy;
$R^4$ and $R^5$ which can be the same or different, are hydrogen, —$NR^6R^7$, fluorine, chlorine, bromine, nitro, —$CF_3$, —CN, —$OR^8$, $C_1$–$C_4$-alkyl, phenyl, benzyl, or phenyloxy;
$R^6$ is hydrogen, $C_3$–$C_6$-cycloalkyl or $C_1$–$C_4$-alkyl, each of them being optionally substituted one or more times with hydroxy, phenyl, benzyl, or $C_1$–$C_4$-alkoxy, or
$R^6$ is phenyl optionally substituted with fluorine, chlorine, bromine, —$OR^8$, or $C_1$–$C_4$-alkyl;
$R^7$ is hydrogen, $C_3$–$C_6$-cycloalkyl or $C_1$–$C_4$-alkyl, each of them being optionally substituted one or more times with hydroxy, phenyl, benzyl, or $C_1$–$C_4$-alkoxy, or
$R^7$ is phenyl optionally substituted with fluorine, chlorine, bromine, —$OR^8$, or $C_1$–$C_4$-alkyl; or,
$R^6$ and $R^7$ together with the nitrogen atom form a 5- or 6-membered ring, saturated or unsaturated, which can contain other heteroatoms selected from nitrogen, oxygen and sulfur, wherein the heterocycle can be substituted with $C_1$–$C_4$-alkyl, phenyl, or benzyl; and, $R^8$ is hydrogen, $C_1$–$C_4$-alkyl, a benzyl or phenyl residue, optionally substituted one or more times with hydroxy, chlorine, bromine, or methoxy, or a pharmaceutically acceptable salt thereof.

2. The compound of the formula (I), according to claim 1, wherein:
A is a triazine optionally substituted one or more times with $=O$ or $C_1$–$C_4$-alkyl;
X is oxygen;
$R^1$ is $C_1$–$C_4$-alkyl substituted with —$NR^6R^7$ or with an N-oxide of formula —$NOR^6R^7$;
$R^2$ and $R^3$ are hydrogen;
$R^4$ and $R^5$ are hydrogen;
$R^6$ is hydrogen or $C_1$–$C_4$-alkyl;
$R^7$ is hydrogen or $C_1$–$C_4$-alkyl; or
$R^6$ and $R^7$ together with the nitrogen atom form a saturated or unsaturated ring selected from the group consisting of pyrrole, pyrroline, pyrrolidine, piperidine, piperazine, morpholine, thiomorpholine, imidazole, imidazoline, imidazolidine, pyrazole, pyrazoline, and pyrazolidine, wherein the cited heterocycles can optionally be substituted with methyl, ethyl, propyl, or benzyl; or a pharmaceutically acceptable salt thereof.

3. The compound of the formula (I), according to claim 1, wherein:
A is a triazine optionally substituted with $=O$ or $C_1$–$C_4$-alkyl;
X is oxygen;
$R^1$ is methyl, ethyl, or propyl, substituted with —$NR^6R^7$ or with an N-oxide of formula —$NOR^6R^7$;
$R^2$ and $R^3$ are hydrogen;
$R^4$ and $R^5$ are hydrogen;
$R^6$ is hydrogen, methyl, ethyl, or propyl; and,
$R^7$ is hydrogen, methyl, ethyl, or propyl; or a pharmaceutically acceptable salt thereof.

4. The compound of the formula (I), according to claim 1, wherein: the moiety of the formula:

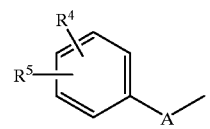

is selected from the group consisting of:

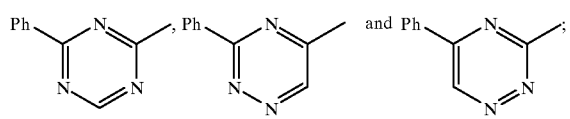

X is oxygen;
$R^1$ is ethyl or propyl, substituted with —$NR^6R^7$;
$R^2$ and $R^3$ are hydrogen; $R^6$ is methyl, ethyl, or propyl; and,
$R^7$ is methyl, ethyl, or propyl; or a pharmaceutically acceptable salt thereof.

5. The compound of the formula (I), according to claim 1, wherein: the moiety of the formula:

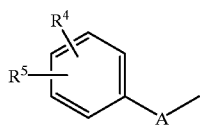

is selected from the group consisting of:

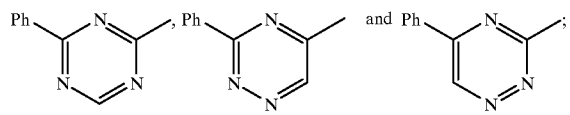

X is oxygen;
$R^1$ is —$CH_2$—$CH_2$—$NR^6R^7$;
$R^2$ and $R^3$ are hydrogen;
$R^6$ is methyl; and
$R^7$ is methyl, or a pharmaceutically acceptable salt thereof.

6. A compound of the formula (I):

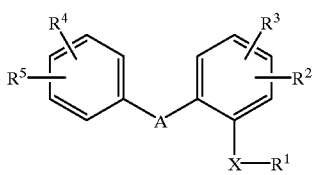

(I)

wherein:
A is a triazine optionally substituted one or more times with =O or $C_1$–$C_4$-alkyl;
X is oxygen;
$R^1$ is a $C_2$–$C_4$-alkyl residue substituted with —$CONHSO_2R^8$, —$CONR^6R^7$, —CH=$NOR^8$, —$NR^6R^7$, —$NHCOR^8$, —$NHCONR^6R^7$, —$NHCOOR^8$, —$OCONR^6R^7$, —$SO_2NR^6R^7$, or with an N-oxide of formula —$NOR^6R^7$;
$R^2$ and $R^3$ which can be the same or different, are hydrogen, —$NR^6R^7$, fluorine, chlorine, bromine, nitro, —$CF_3$, —CN, —$OR^8$, $C_1$–$C_4$-alkyl, phenyl, benzyl, or phenyloxy;
$R^4$ and $R^5$ which can be the same or different, are hydrogen, —$NR^6R^7$, fluorine, chlorine, bromine, nitro, —$CF_3$, —CN, —$OR^8$, $C_1$–$C_4$-alkyl, phenyl, benzyl, or phenyloxy;
$R^6$ is hydrogen, $C_3$–$C_6$-cycloalkyl or $C_1$–$C_4$-alkyl, each of them being optionally substituted one or more times with hydroxy, phenyl, benzyl, or $C_1$–$C_4$-alkoxy, or
$R^6$ is phenyl optionally substituted with fluorine, chlorine, bromine, —$OR^8$, or $C_1$–$C_4$-alkyl;
$R^7$ is hydrogen, $C_3$–$C_6$-cycloalkyl or $C_1$–$C_4$-alkyl, each of them being optionally substituted one or more times with hydroxy, phenyl, benzyl, or $C_1$–$C_4$-alkoxy, or
$R^7$ is phenyl optionally substituted with fluorine, chlorine, bromine, —$OR^8$, or $C_1$–$C_4$-alkyl; or,
$R^6$ and $R^7$ together with the nitrogen atom form a 5- or 6-membered ring, saturated or unsaturated, optionally containing other heteroatoms selected from nitrogen, oxygen and sulfur, wherein the heterocycle can be substituted with $C_1$–$C_4$-alkyl, phenyl, or benzyl; and,
$R^8$ is hydrogen, $C_1$–$C_4$-alkyl, a benzyl or phenyl residue, optionally substituted one or more times with hydroxy, chlorine, bromine, or methoxy, or a pharmaceutically acceptable salt thereof.

7. The compound of the formula (I), according to claim 6, wherein:
A is a triazine optionally substituted one or more times with =O or $C_1$–$C_4$-alkyl;
X is oxygen;
$R^1$ is $C_2$–$C_4$-alkyl substituted with —$NR^6R^7$ or with an N-oxide of formula —$NOR^6R^7$;
$R^2$ and $R^3$ are hydrogen;
$R^4$ and $R^5$ are hydrogen;
$R^6$ is hydrogen or $C_1$–$C_4$-alkyl;
$R^7$ is hydrogen or $C_1$–$C_4$-alkyl; or
$R^6$ and $R^7$ together with the nitrogen atom form a saturated or unsaturated ring selected from the group consisting of pyrrole, pyrroline, pyrrolidine, piperidine, piperazine, morpholine, thiomorpholine, imidazole, imidazoline, imidazolidine, pyrazole, pyrazoline, and pyrazolidine, wherein the cited heterocycles can optionally be substituted with methyl, ethyl, propyl, or benzyl; or a pharmaceutically acceptable salt thereof.

8. The compound of the formula (I), according to claim 6, wherein:
A is triazine optionally substituted with =O or $C_1$–$C_4$-alkyl;
X is oxygen;
$R^1$ is ethyl or propyl, each of them is substituted with —$NR^6R^7$ or with an N-oxide of formula —$NOR^6R^7$;
$R^2$ and $R^3$ are hydrogen;
$R^4$ and $R^5$ are hydrogen;
$R^6$ is hydrogen, methyl, ethyl, or propyl; and,
$R^7$ is hydrogen, methyl, ethyl, or propyl; or a pharmaceutically acceptable salt thereof.

9. A pharmaceutical composition comprising an effective amount of the compound in accordance with one of claims 1 to 5.

10. A pharmaceutical composition comprising an effective amount of the compound in accordance with one of claims 6 to 8.

11. A method for treating or inhibiting damage to the brain due to hypoxia or ischemia which comprises administering to a host suffering from hypoxia or cerebral ischemia, a therapeutic amount of the compound in accordance with one of claims 1 to 5.

12. A method for treating or inhibiting damage to the brain due to hypoxia or ischemia which comprises administering to a host suffering from hypoxia or cerebral ischemia, a therapeutic amount of the compound in accordance with one of claims 6 to 8.

* * * * *

UNITED STATES PATENT AND TRADEMARK OFFICE
CERTIFICATE OF CORRECTION

PATENT NO.    : 6,235,738 B1
DATED         : May 22, 2001
INVENTOR(S)   : Michael Brenner, Rainer Palluk, Marion Weinrich, Thomas Weiser, Enzo Cereda, Maura Bignotti, Carlo Maria Pellegrini, Giovanni Battista Schiavi and Raffaele Cesana It is certified that error appears in the above-identified patent and that said Letters Patent is hereby corrected as shown below:

<u>Column 11,</u>
Line 67, "disfunctions" should read -- dysfunctions --

<u>Column 12,</u>
Line 24, "eccitatory" should read -- excitatory --

<u>Column 16,</u>
Line 61, reads "$R^2$ and $R^3$ are hydrogen, $R^6$ is methyl, ethyl, or propyl; and," should read
-- $R^2$ and $R^3$ are hydrogen,
$R^6$ is methyl, ethyl, or propyl; and, --

Signed and Sealed this

Fourth Day of June, 2002

Attest:

Attesting Officer

JAMES E. ROGAN
Director of the United States Patent and Trademark Office